(12) United States Patent
De La Torre-Montemayor

(10) Patent No.: US 9,828,439 B2
(45) Date of Patent: Nov. 28, 2017

(54) HYBRID VEGETABLE PROTEIN AND METHOD FOR OBTAINING SAME

(71) Applicant: INDUSTRIAS NUTRIGRAINS, S.A., DE C.V., Nuevo Leon (MX)

(72) Inventor: José De La Torre-Montemayor, Nuevo León (MX)

(73) Assignee: INDUSTRIAS NUTRIGRAINS, S.A., DE C.V., Monterrey, Neuvo Leon (MX)

( * ) Notice: Subject to any disclaimer, the term of this patent is extended or adjusted under 35 U.S.C. 154(b) by 0 days.

(21) Appl. No.: 14/870,478

(22) Filed: Sep. 30, 2015

(65) Prior Publication Data

US 2016/0017060 A1    Jan. 21, 2016

Related U.S. Application Data

(62) Division of application No. 13/255,396, filed as application No. PCT/IB2009/000503 on Mar. 12, 2009, now Pat. No. 9,481,737.

(51) Int. Cl.

| C07K 19/00 | (2006.01) |
|---|---|
| A23J 1/14 | (2006.01) |
| A23J 3/16 | (2006.01) |
| C07K 1/107 | (2006.01) |
| C07K 1/14 | (2006.01) |
| C07K 1/12 | (2006.01) |
| A23J 1/12 | (2006.01) |
| A23J 3/14 | (2006.01) |
| A23J 3/32 | (2006.01) |

(52) U.S. Cl.
CPC .............. *C07K 19/00* (2013.01); *A23J 1/12* (2013.01); *A23J 1/14* (2013.01); *A23J 3/14* (2013.01); *A23J 3/16* (2013.01); *A23J 3/32* (2013.01); *C07K 1/107* (2013.01); *C07K 1/12* (2013.01); *C07K 1/145* (2013.01)

(58) Field of Classification Search
None
See application file for complete search history.

(56) References Cited

U.S. PATENT DOCUMENTS

| 5,410,021 A * | 4/1995 | Kampen ............... C08B 30/044 127/67 |
|---|---|---|
| 5,580,959 A | 12/1996 | Cook et al. |
| 2009/0069542 A1* | 3/2009 | Yang ..................... A23J 1/12 530/373 |

FOREIGN PATENT DOCUMENTS

| WO | 2007044886 A2 | 4/2007 |
|---|---|---|
| WO | 2007118935 A1 | 10/2007 |
| WO | 2008011516 A2 | 1/2008 |
| WO | WO 2008/011516 * | 1/2008 ............... A23J 3/00 |

OTHER PUBLICATIONS

Cohn et al., Journal of General Physiology (1919) 145-160.
Gonzalez-Perez et al., "Vegetable Protein Isolates", Chapter 15, Handbook of Hydrocolloids, Phillips and Williams, ed. Oxford:u Woodhead Publishing, 2009. Website: http://f3.tiera.ru/3/Chemistry/Physical%20chemistry/Surface%20and%20Colloid/Phillips%20G.0.,%20Williams%20P.A.%20(eds.)%20Handbook%20of%20hydrocolloids%20(2ed.,%20CRC,%202009)(1SBN%2018.

* cited by examiner

*Primary Examiner* — Marcela M Cordero Garcia
*Assistant Examiner* — Catherine Mader
(74) *Attorney, Agent, or Firm* — Browdy and Neimark, PLLC

(57) ABSTRACT

A hybrid vegetable protein is described, comprising a guest protein having the structure of prolamine and glutelin, and a host protein having the structure of globulin and albumin, obtained from vegetable grains, such as corn and soybean, respectively. Likewise, a method for obtaining said hybrid vegetable protein is described, which comprises the steps of extracting the guest and host proteins, carrying out an acidification thereof, and further applying a magnetic field to provoke their attachment, and finally adding an alkali to the attached proteins to obtain a hybrid vegetable protein at its isoelectric point. The protein thus produced has a value higher than 0.97 according to the PDCAAS rating.

20 Claims, 2 Drawing Sheets

HYBRID VEGETABLE PROTEIN AND METHOD FOR OBTAINING SAME

TECHNICAL FIELD

The present invention relates to the techniques employed in protein obtaining from vegetal grains in the Feeding Industry, and more particularly, it refers to a hybrid vegetable protein formed from at least one guest protein, having the structure of prolamine and glutelin, and at least one host protein, having the structure of globulin and albumin, to which the guest protein attaches to, and which nutritional value is higher than that of the guest protein. In addition, the invention is related to the physical-chemical method to produce said hybrid vegetable protein.

BACKGROUND OF THE INVENTION

The name protein comes from the Greek "proteios" meaning "first" since they have the highest importance between the molecules conforming the living beings. In vertebrates, proteins are the most abundant organic compounds, representing about 50% of the tissues, in a dry basis.

Practically, all biological processes depend on the presence and/or activity of these types of substances. Almost all enzymes, chemical reaction catalysts in living organisms, are proteins; many hormones, regulators of cellular activities; the hemoglobin and other molecules with transport functions in the blood; antibodies, in charge of natural defense actions against infections or foreign agents; cells receptors, to which molecules capable of developing a determined response are affixed to; actine and miosine, final responsible of the muscle shortening during a contraction; collagen, integrant of highly resistant fibers in holding tissues; these are only some examples to provide an idea of the variety and transcendence of their assigned functions.

Proteins are macro-molecules formed by amino acid chains, which are molecules having a free carboxyl group (—COOH) and a free amino group (—$NH_2$). In all amino acid conforming proteins, except glycine, the alpha carbon is an asymmetrical carbon. There are about 20 different amino acids conforming proteins. The chemical bonding between amino acids in proteins is made by a peptide linkage. Hundreds and thousands of these amino acids can participate forming one protein molecule.

According to the protein shape, these may be classified in fibroses and globular, wherein the former have long amino acid chains, keratin and collagen are examples thereof. On the other hand, globular proteins are characterized by bending their chains in a tight or compacted spherical shape, such as most enzymes, antibodies, some hormones and transport proteins.

From the standpoint of human nutrition, protein consumption including the so called essential amino acids is vital, as the lack of these amino acids limits the organism development as being non-capable to replenish dead cells and tissues or to create new ones. Essential amino acids are: Valine (Val), Leucine (Leu), Isoleucine (Ile), Phenylalanine (Phe), Methionine (Met), Threonine (Thr), Lysine (Lys), Tryptophan (Trp), and Histidine (His).

Likewise, there are amino acids capable of being synthesized by the body, and they are referred as non-essential, these being: Arginine (Arg), Alanine (Ala), Proline (Pro), Glycine (Gly), Serine (Ser), Cysteine (Cys), Asparagine (Asn), Glutamine (Gln), Tyrosine (Tyr), Aspartic acid (Asp), and Glutamic Acid (Glu).

The human body synthesizes the non-essential amino acids, while those essential have to be provided by food. All animal and vegetal proteins have about the same 20 amino acids. The amino acids ratio varies as a function of the protein source. Nutritional quality of any protein is related to its amino acid composition, digestibility, and capability to supply essential amino acids in the required amounts to those organisms consuming the protein.

In order to evaluate the protein quality, traditionally the reference standard value referred as Protein Efficiency Ratio (PER) was used. The PER method reflects the amino acids requirements of young growing rats and not of human beings. However, in 1991, the experts of the Joint Consultative Meeting of the Food and Agriculture Organization of the United Nations, and the World Health Organization (FAO/WHO), published a report requesting the search of a more adequate and validated procedure for the protein quality evaluation, "Protein Digestibility Corrected Amino Acid Score" (PDCAAS), which has been accepted by the Food and Drugs Administration (FDA) in the United States for the evaluation of the protein quality and the labeling with nutritional information of products directed to children older than 2 years.

The PDCAAS is based in an amino acid scoring method, wherein the amino acid profile of the tested protein food is compared versus the amino acid requirement pattern established by the FAO/WHO for children between two and five years old. This pattern corresponding to children between two and five years old is used since they overcome the amino acid requirement pattern of older children and adults. The amino acid with a boundary value is used to establish the non-corrected amino acid score, and by multiplying said number by the food digestibility, the PDCAAS is obtained.

According to this method, the soy isolated proteins reach the maximum possible score (1.0) for the calculation of the corrected protein value. Any protein may have a PDCAAS value higher than 1.0. Soy proteins are complete proteins, highly digestible having all essential amino acids of the reference model in the right ratio. The pattern recommended by the FAO for proteins according to the PDCAAS is shown In Table 1.

TABLE 1

|  | FAO/WHO pattern for 2 to 5 years old children Mg/g protein |
|---|---|
| Histidine | 19 |
| Isoleucine | 28 |
| Leucine | 66 |
| Lysine | 58 |
| Methionine + Cysteine | 25 |
| Phenylalanine + Tyrosine | 63 |
| Threonine | 34 |
| Tryptophan | 11 |
| Valine | 35 |

In view of the above, there is always a need to develop feeding compositions and methods providing essential amino acids for human consumption. In the prior art, for example, in U.S. Pat. No. 4,054,677, a process to prepare vegetable protein concentrates, products produced therefrom and milk containing said concentrates as food substitute, are described. The method comprises the steps of: subjecting a weak acid and vegetal flour having protein contents to hydrolysis; subjecting an alkali with the vegetal flour having protein contents to hydrolysis; mixing both hydrolyzed solutions and neutralizing them up to a pH of between 6.7 and 7.1; concentrating the neutralized mixture until obtaining a low dry matter concentration, and then drying again. However, it is observed that a limiting feature in said process is that proteins are produced from flours, which are products derived from grains having to be processed, which increases the costs of the produced product in said patent.

A prior art process to obtain recombinant proteins is disclosed in U.S. Pat. No. 7,229,792, wherein the object is to achieve the proteins or polypeptides production during the growing of bacterial or other host cells, substantially culturing them on a solid or semi-solid nutrition media and including the DNA sequences of concern to codify the recombinant proteins under the control of an inducing-regulating promoter or a constitutive promoter. Bacteria are feed from a solid or semi-solid nutrition media and the recombinant protein to be produced is recovered by irrupting the bacteria's surface. As can be seen, this process requires living organisms, which are both sensitive to the media and highly specific, then requiring more controllable processes which allow the large-scale production of hybrid proteins.

Likewise, in the U.S. Patent Application No. 2004/0086613, hydro-thermal processes are shown, to prepare hybrid proteins having modified SS/SH bonds, thereby producing hybrid proteins having remarked functional properties. Such processes involve a treatment with steam of an aqueous protein solution having admixed at least two different proteins, in a heating device provoking a thermal shock and thus altering the protein conformation, followed by a relatively fast cooling to provoke the formation of the desired hybrids. By the process disclosed in said application, both animal and vegetal proteins may be processed, and the starting mixture might be modified in its pH value and/or supplemented with one or more additional ingredients such as salts, phosphates, fatty acids, polysaccharides, alcohols, aromatic compounds. However, there is the great inconvenience that said procedure is expensive from the standpoint of energetic consume, due to the use of steam, besides, the thermal shocks and the abrupt temperature changes may degrade the obtained protein.

Due to the drawbacks of the procedures found in the prior art for the production of proteins, as described above, a simple, practical and economic manner to overcome said drawbacks has been looked for, by developing a procedure which allows the large-scale obtaining of high nutritional value proteins, mainly by using accessible vegetal origin sources.

BRIEF DESCRIPTION OF THE INVENTION

Accordingly, suppressing the prior art drawbacks has been looked for by developing a hybrid vegetable protein comprising at least one guest protein having the structure of prolamine and glutelin, with an isoelectric point between 5.2 and 6.6, and a molecular weight from 37 to 46 kD, and at least one host protein having the structure of globulin and albumin, with an isoelectric point of between 4.0 and 5.0, and a molecular weight from 100 to 120 kD, to which the guest protein is attached to, wherein the ratio between the guest protein and the host protein is between 3:1 and 4:2, and preferably 3:1.

The guest and host proteins are produced from vegetal grains, and more preferably, the guest protein is produced from corn grains; while the host protein is obtained from soybean grains. The PDCAAS value in the hybrid protein of the present invention is of at least 0.97.

In other aspect of the invention, a method for the obtaining of the hybrid vegetable protein is described, which comprises the steps of extracting and hydrolyzing at least one host protein and at least one guest protein from vegetal grains; acidifying the proteins extracted in the previous step; applying a magnetic field to the acidified proteins in order to open the amino acid chain of the guest protein to be received in the amino acid chain of the host protein, thereby forming a hybrid protein out of its isoelectric point; and, finally, adding an alkali to the hybrid protein to take it to its isoelectric point thus obtaining an stabilized hybrid protein.

In a first alternative embodiment of the hybrid vegetable protein obtaining method of the present invention, said method further comprises the step of grinding the guest and host proteins previously acidified, at the same time of applying the magnetic field.

Likewise, in a second alternative embodiment of the hybrid vegetable protein obtaining method of the present invention, said method further comprises a drying step, preferably spray-drying, carried out after the alkali addition.

BRIEF DESCRIPTION OF THE FIGURES

The novel aspects considered characteristic of the present invention are particularly established in the appended claims, however, the structure of the hybrid vegetable protein, as well as the integration of the method steps for the obtaining thereof, will be better understood from the following detailed description of certain embodiments when read related to the appended drawings, wherein:

DETAILED DESCRIPTION OF THE EMBODIMENTS OF THE INVENTION

Figure 1:
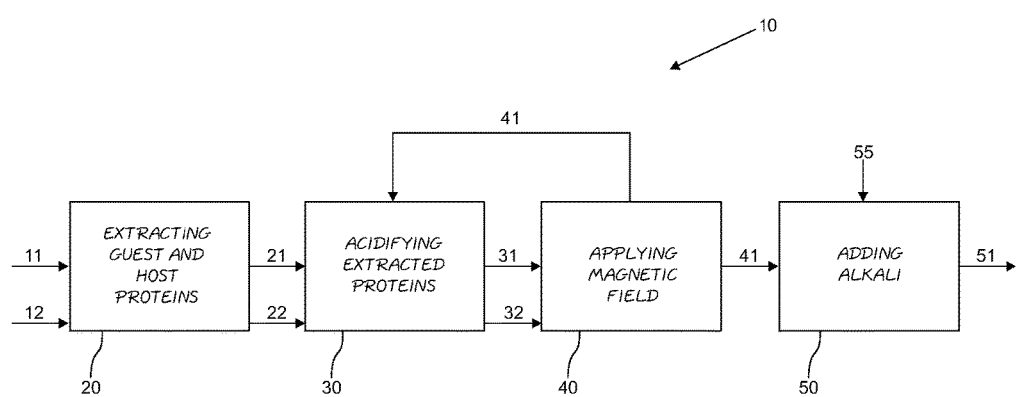
FIG. 1 is a block diagram showing the step sequence of a method for the hybrid vegetable proteins obtaining, developed according to the principles of a particularly specific embodiment of the present invention.

The hybrid vegetable protein 51 claimed in the present invention comprises: at least one guest protein 21 having a structure of prolamine and glutelin, obtained from a first grain 11, having an isoelectric point of between 5.2 and 6.6, and a molecular weight from 37 kD to 46 kD; and at least one host protein 22 having a structure of globulin and albumin, obtained from a second grain 12, having an isoelectric point of between 4.0 and 5.0, and a molecular weight from 100 kD to 120 kD, wherein the guest protein 21 structure opens to facilitate its attachment to the amino acid chain of the host protein 22.

The first grain 11 used as a source of the guest protein 21, is selected from corn, wheat, sorghum, rye, quinoa, amaranth, among others; most preferably using corn grains.

For the first corn grain 11, preferably the germ of the seed is used, since as shown in Table 2, main parts of the corn grain 11 substantially differ in its chemical composition, for example, the seed cover or pericarp is characterized by a high content of crude fiber (about 87%), which in turns is mainly formed by hemicellulose (67%), cellulose (23%) and lignin (0.1%). On the contrary, the endosperm has a high level of starch (87%), about 8% proteins and a relatively small crude fat content. Finally, the germ is characterized by a high crude fat content, with an average of 33%, and also having a relatively high level of proteins near to 20%.

TABLE 2

Approximate chemical composition of the main parts in corn grains (%)

| Chemical component | Pericarp | Endosperm | Germ |
| --- | --- | --- | --- |
| Proteins | 3.7 | 8.0 | 18.4 |
| Ethereal extract | 1.0 | 0.8 | 33.2 |
| Crude fiber | 86.7 | 2.7 | 8.8 |
| Ashes | 0.8 | 0.3 | 10.5 |
| Starch | 7.3 | 87.6 | 8.3 |
| Sugar | 0.34 | 0.62 | 10.8 |

On the other hand, the second grain 12 used as the host protein 22 source is selected from soybean, safflower, sunflower, olive, canola, among others; using preferably soybean grains.

Regarding the second grain 12 preferred to obtain the host protein 22, soybean is preferred to use. Soy isolated proteins are obtained by an extraction process with water and applying a minimum temperature over the soybean flakes. This product practically does not contain carbohydrates or fat, and does not have the peculiar "leguminous" flavor of the soybean grains. Soy protein isolates are 90% protein in a dry basis, the concentration of the soy protein amino acids can be seen in Table 3.

TABLE 3

| | Soy protein mg/g protein |
| --- | --- |
| Histidine | 26 |
| Isoleucine | 49 |
| Leucine | 82 |
| Lysine | 63 |
| Methionine + Cysteine | 26 |
| Phenylalanine + Tyrosine | 90 |
| Threonine | 38 |
| Tryptophan | 13 |
| Valine | 50 |

The ratio between the guest protein 21 and the host protein 22 is of between 3:1 and 4:2, and preferably is of 3:1. Likewise, the PDCAAS value in the hybrid vegetable protein 51 of the present invention is of at least 0.97.

Each gram of hybrid vegetable protein has a minimum concentration value of the following amino acids: 50 mg isoleucine, 102 mg leucine; 50 mg lysine; 35 mg cysteine; 95 mg tyrosine; 42 mg threonine; 10 mg tryptophan and 56 mg valine.

Now referring to FIG. 1 of the appended drawings, the method 10 for the hybrid vegetable protein obtaining 51 of the present invention starts with step 20, wherein the extraction and hydrolysis of the guest protein 21 and host protein 22 is made from the first and second grains 11 and 12, respectively.

Further, the extracted guest and host proteins 21 and 22, respectively, are acidified with sulfuric acid ($H_2SO_4$) in step 30, at a pH of between 3 and 5, at a temperature of between 40 and 50° C., and more preferably, the acidification temperature is from 43° to 47° C. In this step the acidified guest and host proteins 31 and 32, respectively, are obtained.

In step 40, a magnetic field is applied to the guest 31 and host 32 acidified proteins, in order to open the amino acid chain of said acidified guest protein 31 and to provoke its attachment to the acidified host protein 32, thereby obtaining a hybrid vegetable protein 41, out of its isoelectric point.

Continuing with the block diagram description of FIG. 1, an alkali 55 is added in step 50, to provoke that the hybrid vegetable protein 41 reaches its isoelectric point, thereby obtaining the hybrid vegetable protein 51 in solution, which can de used in various food compositions.

Figure 2:
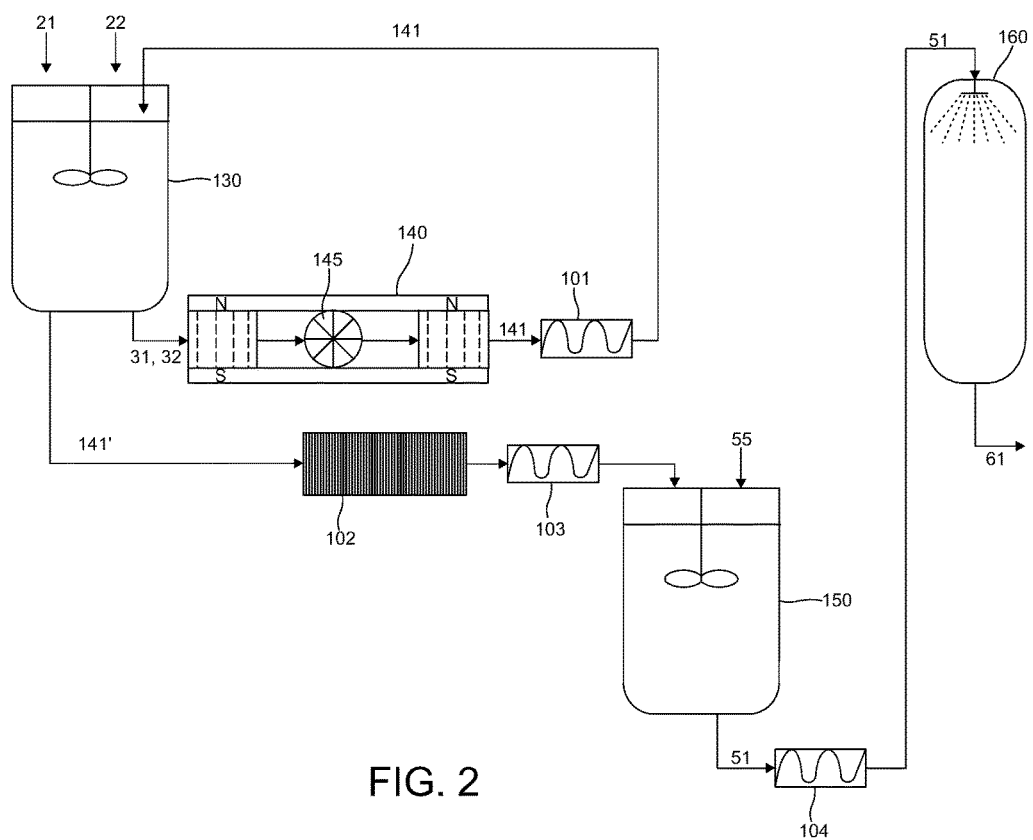
FIG. 2 is a flowchart showing the step sequence of the method for the hybrid vegetable proteins obtaining, developed according to the principles of a first alternative embodiment of the present invention.

Now, referring to FIG. 2 of the appended drawings, and wherein a flowchart of the method for the hybrid vegetable protein 61 obtaining is shown, according to a first alternative embodiment of the present invention, wherein, particularly, in the mixing tank 130 the already extracted guest protein 21 and host protein 22 are acidified, wherein the acidification is carried out preferably at a temperature between 43 and 47° C., as mentioned above. From the mixing tank 130 bottom, the guest 31 and host 32 acidified proteins are extracted, which are subjected to a magnetic field generated by a magnet 140, wherein the generated magnetic field has a value of 2450 gauss to 3850 gauss. The magnet used is preferably made of $Nd_2Fe_{14}B$.

In the first alternative embodiment being described, at the same time the magnetic field is applied to the guest 31 and host 32 acidified proteins, these are subjected to an additional grinding step in a colloidal grinder 145, which favors even more the attachment between both proteins.

After passing through the magnet 140, the obtained product is a hybrid vegetable protein 141 out of its isoelectric point, which is then passed through a pump 101 which sends the hybrid vegetable protein 141 to the mixing tank 130 to be recirculated for 30 to 60 minutes, in order to maintain the maximum ionization, and to obtain the highest hybridization yielding, thus producing an optimized hybrid vegetable protein 141'; further the hybrid vegetable protein 141 ' is conveyed to a filter press 102 to remove residues and impurities. From said filter press 102, the hybrid vegetable protein 141' is fed to a second pump 103 which sends it to a neutralization tank 150, wherein an alkali 55 is added, preferably calcium or sodium hydroxide and more preferably, by using calcium hydroxide. When adding the alkali 55, a hybrid vegetable protein in solution 51 at its isoelectric point is obtained. Said hybrid vegetable protein in solution 51 is conveyed by a pump 104 to a spray-dryer 160, wherein the protein 51 is dried at a temperature of between 140° and 180° C., thereby producing the dried hybrid vegetable protein 61, which has obvious advantages, since its transportation and further processing is cheaper than keeping it in solution.

The hybrid vegetable protein 61 and its obtaining method will be more clearly illustrated by means of the following description of examples, which are provided only with illustrative purposes, and not to limit the scope of the present invention.

EXAMPLE 1

Hybrid Vegetable Protein Obtaining Using Corn Germ and Soy Protein 3 kg of corn germ and 1 kg of soy protein were used, soaked for at least 3 hours at 45° C., using 3 liters of water per each kg of dry matter; then sulfuric acid ($H_2SO_4$) was added to acidify the guest and host proteins up to the required pH; immediately after, the grinding was carried out at the same time that the magnetic field was applied, recirculating to the acidification step all protein subjected to the magnetic field; then, the hybrid vegetable protein was passed through a filter press wherein all the grain was removed; the liquid was transferred to another vessel wherein the product was neutralized with calcium hydroxide (Ca(OH)$_2$); the waste materials were removed by decantation; then spray-drying was carried out at a drying temperature of between 140° and 180° C.; finally, the product was dry packaged.

Table 4 shows the comparative results between the PDCAAS rating obtained for protein sources, and those achieved in this Example 1 of the present invention. Also included for reference are the FAO recommended values.

TABLE 4

| Source | AMINO ACID | | | | | | | | PDCAAS rating |
|---|---|---|---|---|---|---|---|---|---|
| | Ile | Leu | Lys | Cys | Tyr | Thr | Trp | Val | |
| FAO/WHO | 40 | 70 | 55 | 35 | 60 | 40 | 10 | 50 | 1.00 |
| Egg | 54 | 86 | 70 | 57 | 93 | 47 | 17 | 66 | 1.00 |
| Casein | 64 | 101 | 79 | 34 | 112 | 44 | 14 | 72 | 0.97 |
| H corn | 47 | 132 | 29 | 32 | 107 | 40 | 6 | 52 | 0.53 |
| H soy | 53 | 77 | 63 | 32 | 82 | 40 | 14 | 52 | 0.91 |
| Rice | 52 | 86 | 38 | 36 | 92 | 38 | 10 | 66 | 0.69 |
| Example 1 | 50 | 102 | 50 | 35 | 95 | 42 | 10 | 56 | 0.97 |

Although in the above description certain embodiments of the present invention have been shown and described, it must be remarked that numerous modifications are possible, such as, but not limited to, the guest and host protein source, the magnet type. Therefore, the present invention shall not be restricted except for that established in the state of the art, and by the appended claims.

The invention claimed is:

1. A method for obtaining a hybrid vegetable protein, comprising the steps of:
   a) extracting and hydrolyzing at least a first protein, and at least a second protein, from a first and second vegetable source, respectively, in order to obtain hydrolyzed proteins;
   b) acidifying the hydrolized proteins, in order to obtain acidifed proteins;
   c) applying a magnetic field to the acidified proteins in order to open the amino acid chain of the first protein to be received in the amino acid chain of the second protein, thereby forming a hybrid vegetable protein at a pH value which does not correspond to the isoelectric point of said hybrid vegetable protein; and,
   d) adding an alkali to the hybrid protein to take it to its isoelectric point, and thus producing a stable hybrid vegetable protein.

2. The method for obtaining a hybrid vegetable protein according to claim 1, wherein step b) is carried out using sulfuric acid.

3. The method for obtaining a hybrid vegetable protein according to claim 1, wherein step b) is carried out at a temperature of between 40° and 50 ° C.

4. The method for obtaining a hybrid vegetable protein according to claim 1, wherein step b) is carried out at a temperature of between 43° and 47 ° C.

5. The method for obtaining a hybrid vegetable protein according to claim 1, wherein the magnetic field applied in step c) is in the range of between 2450 gauss and 3850 gauss.

6. The method for obtaining a hybrid vegetable protein according to claim 1, further comprising a grinding step of the first and second acidified proteins at the same time of applying the magnetic field in step c).

7. The method for obtaining a hybrid vegetable protein according to claim 6, wherein a colloidal grinder is used for grinding.

8. The method for obtaining a hybrid vegetable protein according to claim 1, wherein the magnet used in step c) is of the Nd$_2$Fe$_{14}$B type.

9. The method for obtaining a hybrid vegetable protein according to claim 1, further comprising a drying step of the hybrid protein, after step d).

10. The method for obtaining a hybrid vegetable protein according to claim 9, wherein the drying is carried out by spray-drying.

11. The method for obtaining a hybrid vegetable protein according to claim 9, wherein the drying temperature is of between 140° and 180° C.

12. The method for obtaining a hybrid vegetable protein according to claim 1, wherein the alkali added in step d) is calcium or sodium hydroxide.

13. The method for obtaining a hybrid vegetable protein according to claim 12, wherein the hydroxide is calcium hydroxide.

14. The method for obtaining a hybrid vegetable protein according to claim 1, wherein the protein having been subjected to the magnetic field is recirculated to the acidification step for 30 to 60 minutes in order to maintain the maximum ionization and to obtain the highest yielding in the hybridization of the vegetable protein.

15. The method for obtaining a hybrid vegetable protein according to claim 1, wherein the first protein is obtained from a first vegetal source selected from corn, wheat, sorghum, rye, quinoa, and amaranth.

16. The method for obtaining a hybrid vegetable protein according to claim 15, wherein the first vegetal source is corn grain.

17. The method for obtaining a hybrid vegetable protein according to claim 16, wherein the protein is produced from the germ of the corn grain.

18. The method for obtaining a hybrid vegetable protein according to claim 1, wherein the second protein is obtained from a second vegetal source selected from soybean, safflower, sunflower, olive, and canola.

19. The method for obtaining a hybrid vegetable protein according to claim 18, wherein the second vegetal source is soybean grain.

20. The method for obtaining a hybrid vegetable protein according to claim 1, wherein the first protein is obtained from corn grains and the second protein is obtained from soybean grains.

* * * * *